(12) United States Patent
Fagan et al.

(10) Patent No.: US 7,970,630 B2
(45) Date of Patent: Jun. 28, 2011

(54) INTEGRATED BIOMEDICAL INFORMATION PORTAL SYSTEM AND METHOD

(75) Inventors: Andrew Thomas Fagan, Apex, NC (US); Lauren A. B. Bond, Apex, NC (US); Andrew Joseph Foglia, Holly Springs, NC (US); Martin Francis Michael, Chapel Hill, NC (US); Brian Lee Stratton, Raleigh, NC (US); Peter Alan Villiers, Apex, NC (US)

(73) Assignee: SAS Institute Inc., Cary, NC (US)

( * ) Notice: Subject to any disclaimer, the term of this patent is extended or adjusted under 35 U.S.C. 154(b) by 347 days.

(21) Appl. No.: 12/350,309

(22) Filed: Jan. 8, 2009

(65) Prior Publication Data

US 2009/0132278 A1    May 21, 2009

Related U.S. Application Data

(63) Continuation of application No. 10/014,883, filed on Dec. 11, 2001, now Pat. No. 7,493,265.

(51) Int. Cl.
*G06Q 10/00* (2006.01)
(52) U.S. Cl. .............................................. 705/2; 705/3
(58) Field of Classification Search .................. 705/2–3, 705/7; 707/104.1
See application file for complete search history.

(56) References Cited

U.S. PATENT DOCUMENTS

| | | | |
|---|---|---|---|
| 5,949,999 A | 9/1999 | Song et al. | |
| 6,917,944 B1 | 7/2005 | Prasad et al. | |
| 7,054,823 B1 | 5/2006 | Briegs et al. | |
| 2002/0049738 A1 | 4/2002 | Epstein | |
| 2002/0087673 A1 | 7/2002 | Selkirk et al. | |
| 2003/0028549 A1 | 2/2003 | Hartel et al. | |

FOREIGN PATENT DOCUMENTS

WO    WO 03/021389 A2 *  3/2003

OTHER PUBLICATIONS www.medterms.com (definition of Adverse reaction).*
Perez, Juan Carlos, "Taming the metadata monster", PC Week, vol. 14, No. 7, p. 8, ISSN: 0740-1604, Dialog ID No. 09282884; from Dialog File 148: Gale Group Trade & Industry Database [Feb. 17, 1997].

* cited by examiner

*Primary Examiner* — Vivek D Koppikar
(74) *Attorney, Agent, or Firm* — Jones Day

(57) ABSTRACT

A computer-implemented system and method for integrating data from a plurality of biomedical development phases. The system and method include a database that stores data collected from the biomedical development phases. The database further includes a metadata data structure that describes the data collected during a biomedical development phase. At least one graphical user interface collects data during the biomedical development phase. The structure of the graphical user interface is defined based at least in part upon the metadata data structure so that the graphical user interface collects data points as well as metadata that is to be stored within the metadata data structure. The metadata describes the collected data points, and at least a portion of the metadata data structure is determined based upon an issue that arises in a subsequent biomedical development phase.

36 Claims, 21 Drawing Sheets

| | | |
|---|---|---|
| Administration route: | intravenous drip ▽ | Other: |
| Formulation: | aqueous | |

Data Explorer enabled: ✓

| | |
|---|---|
| Patient column: | studyid.subjid |
| Visit column: | visit |
| Study period column: | |
| Number of periods: | 3 |
| Baseline value of visit: | 0 |
| Titles and Footnotes: | Edit |

Last uploaded from path: G:\UVADATA\nicsah2\shortv8\demo.sas7bdat

| Columns | | | | | |
|---|---|---|---|---|---|
| Name | Label/Description | Type | Length | Format | Informat |
| ☐ age | Age in Years at Baseline | Numeric | 8 | BEST12 | F12. |
| ☐ dmactdy | Actual Day of Visit/Collection/Exam | Numeric | 8 | BEST12 | F12. |
| ☐ HEIGHT | Height in Centimeters | Numeric | 8 | BEST12 | F12. |
| ☐ invname | Investigator Name | Character | 4 | $F4 | $F4 |
| ☐ race | Race | Character | 9 | $F9 | $F9 |
| ☐ sex | Sex | Character | 6 | $F6 | $F6 |
| ☐ studyid | Study ID | Character | 8 | $F8 | $F8 |
| ☐ subjid | Subject ID | Numeric | 8 | BEST12 | F12. |
| ☐ trtcd | Treatment Code | Numeric | 8 | BEST12 | F12. |
| ☐ TRTGRP | Treatment Group | Character | 8 | $F8 | $F8 |
| ☐ WEIGHT | Weight in Kilograms | Numeric | 8 | BEST12 | F12. |

—180 (edit) (add) (delete) (add key)

Default measure definition column:      [NONE] ▽
Default measure definition column type: [NONE] ▽
Default measure grouping column:        [NONE] ▽

| Keys | | | |
|---|---|---|---|
| Key name | Description | Key order | Key sort order |
| ☐ studyid | Study ID | 1 | Ascending |
| ☐ subjid | Subject ID | 2 | Ascending |

Unique by keys?: ☐

Fig. 4

Last uploaded from path: G:\UVADATA\nicsah2\shortv8\adverse.sas7bdat

| Columns | | | | edit | add | delete | add key |
|---|---|---|---|---|---|---|---|
| Name | Label/Description | Type | Length | Format | Informat | | |
| ☐ aecom | Comment | Numeric | 8 | BEST12 | F12. | | |
| ☐ aedecod | AE Decode from Dictionary | Character | 21 | $F21 | $F21 | | |
| ☐ aeout | Outcome of Event | Numeric | 8 | BEST12 | F12. | | |
| ☐ aesev | Severity/Intensity of Event | Numeric | 8 | BEST12 | F12. | | |
| ☐ studyid | Study ID | Character | 8 | $F8 | $F8 | | |
| ☐ subjid | Subject ID | Numeric | 8 | BEST12 | F12. | | |

190 ↙

Default measure definition column: [aedecod ▽]
Default measure definition column type: [Event ▽]
Default measure grouping column: [[NONE] ▽]

192 ↗

| Keys | | | edit | delete |
|---|---|---|---|---|
| Key name | Description | Key order | Key sort order | |
| ☐ studyid | Study ID | 1 | Ascending | |
| ☐ subjid | Subject ID | 2 | Ascending | |

Unique by keys?:  ☐

*Fig. 5*

|  | Treatment Code | | |
|---|---|---|---|
| Summary Variables | 1 (N=181) | 2 (N=184) | Total (N=365) |
| Race | | | |
| Black | 41 (22.7) | 36 (19.6) | 77 (21.1) |
| Caucasian | 130 (71.8) | 138 (75.0) | 268 (73.4) |
| Oriental | 2 (1.1) | 4 (2.2) | 6 (1.6) |
| Other | 8 (4.4) | 6 (3.3) | 14 (3.8) |
| | | | |
| Sex | | | |
| Female | 134 (74.0) | 112 (60.9) | 246 (67.4) |
| Male | 47 (26.0) | 72 (39.1) | 119 (32.6) |
| | | | |
| Weight in Kilograms | | | |
| n | 181 | 184 | 365 |
| Mean | 69.4 | 73.4 | 71.5 |
| Median | 67.0 | 70.0 | 69.0 |
| Std. Dev. | 15.80 | 16.71 | 16.37 |
| Std. Error | 1.17 | 1.23 | 0.86 |
| Minimum | 38 | 42 | 38 |
| Maximum | 149 | 134 | 149 |

Fig. 13

INTEGRATED BIOMEDICAL INFORMATION PORTAL SYSTEM AND METHOD

This is a continuation of U.S. patent application Ser. No. 10/014,883, filed on Dec. 11, 2001 now U.S. Pat. No. 7,493,265.

BACKGROUND OF THE INVENTION

1. Technical Field

The present invention is generally directed to the field of biomedical information analysis, and more particularly to computer methods and systems of accessing biomedical information.

2. Description of the Related Art

Biomedical research data that describe, measure and improve life is becoming the vital exchange medium for all new medical knowledge and the way by which we understand it. However, a resulting culture of point-solution software and services acquisitions, combined with large systems integrators, has created an inefficient tapestry of non-standardized data technology systems with high ongoing maintenance and support costs.

The number of transfers a therapy undergoes during development exacerbates this state of affairs. For instance, many drug compounds are sold or licensed at multiple times. This does not include the myriad exchanges of data and information between the sponsor and its external partners, such as laboratories, independent data review boards and regulatory authorities. As a result, nearly all strategic plans for the world's largest pharmaceutical research firms include provisions for reengineering the data access and analysis model.

The Food and Drug Administration (FDA) is the primary agency of the United States government that oversees the approval process of therapeutic compounds. The FDA requires as part of the approval process meticulous records that allow the agency to review all data generated for a particular compound.

SUMMARY OF THE INVENTION

The present invention solves the aforementioned disadvantages as well as other disadvantages. In accordance with the teachings of the present invention, an Internet-based system and method and process frameworks deploy computer software and deliver biomedical information directly to the medical scientist or regulatory agency. The presented process frameworks of the system and method provide lasting mechanisms for maintaining the rapid flow of analytical knowledge and speeding the collaborative process around biomedical research data by the development of data and biomedical informatics portals attached to drugs, biologics and devices. The system and method may also include genomics data. This unifies information and minimizes the cost of transfer and due diligence expenses associated with new therapies under development.

The system and method provide a common framework for data between the sponsor, development partners, alliance network, research sites and regulatory bodies supporting dialogue among organizations and permits efficient sharing of information about a compound with external partners in a secure environment. When data about a compound is transferred, the system and method provide an efficient transfer mechanism and decreases the cost of scientific due diligence that must be conducted to sell, purchase, build alliances around, regulate, approve or monitor a compound.

BRIEF DESCRIPTION OF THE DRAWINGS

The present invention satisfies the general needs noted above and provides many advantages, as will become apparent from the following description when read in conjunction with the accompanying drawings, wherein:

FIGS. 3-13 are screen images that depict graphical user interfaces associated with acquiring data and metadata;

DETAILED DESCRIPTION

Figure 1:
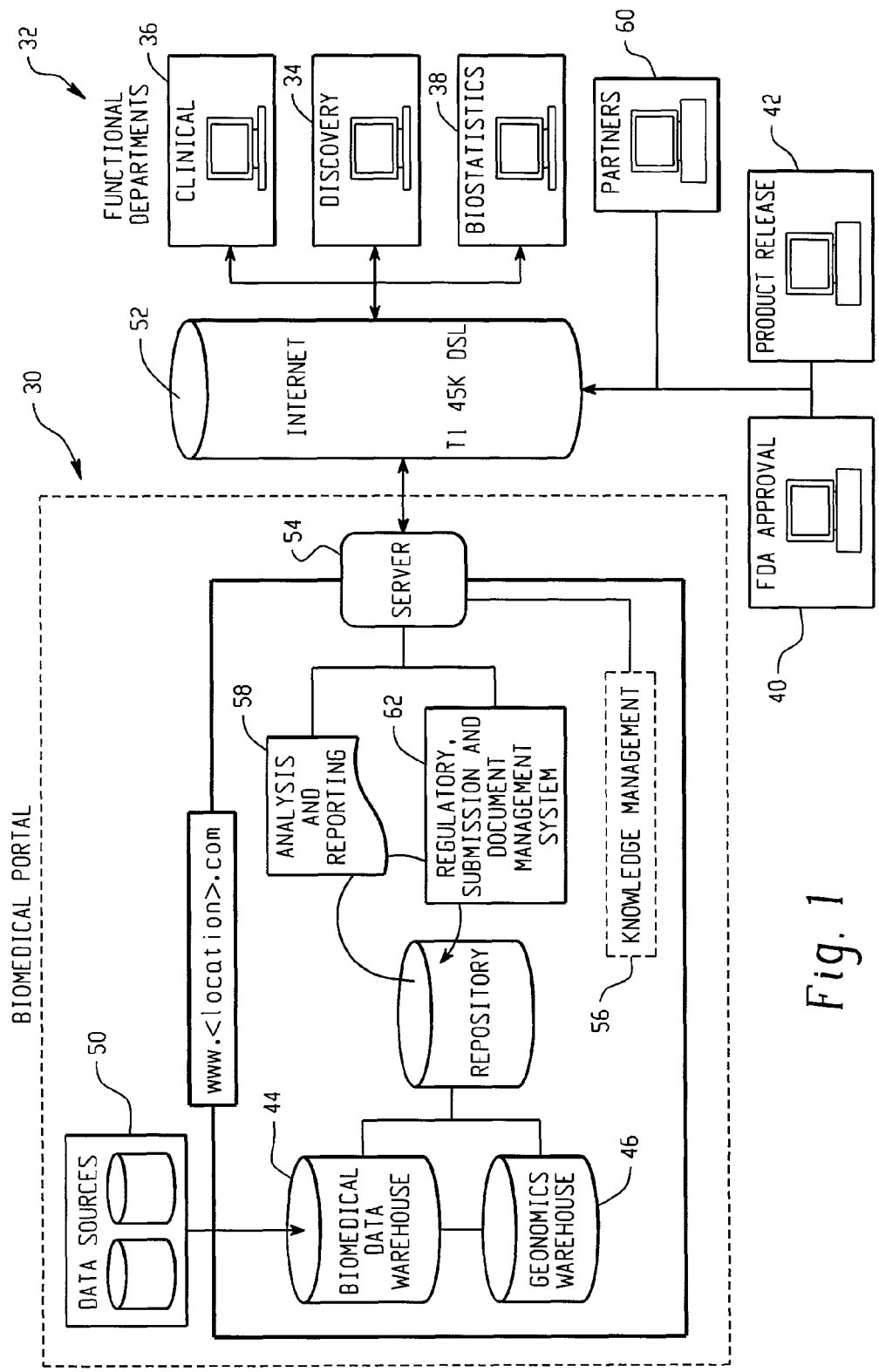
FIG. 1 is system block diagram that depicts a bioinformatics portal system environment.

FIG. 1 depicts a biomedical portal computer system generally at 30. The biomedical portal computer system 30 collects and integrates biomedical data across multiple biomedical development phases. Due to this data integration, life science and pharmaceutical industry scientists can better understand and more rapidly predict the safety and efficacy of such biomedical products as drugs, biologics and medical devices. This better understanding translates into a more coherent reporting of the safety and efficacy of biomedical products to personnel from the Food and Drug Administration (FDA) during the product's approval process.

Various biomedical functional departments 32 use the portal system 30 during the different biomedical development phases. During the discovery phase 34 wherein laboratory testing is performed, the discovery department provides discovery-related data to the biomedical portal system 30. The clinical studies phase 36 uses animal and patient testing to further hone the development of a biomedical product. The biomedical portal system 30 collects the animal and patient testing data. The biostatistics department 38 analyzes the data collected during the phases.

Additional phases' data are also collected, such as data from the FDA approval phase 40 and the product release phase 42. The FDA approval phase 40 not only provides additional data (such as areas of concern identified during the FDA approval phase 40 for the proposed biomedical product) but also uses the data collected and integrated from the previous phases to perform its analysis. The product release phase 42 provides data to the biomedical portal system 30 that relates to how the biomedical product is performing in the field and the circumstances behind any adverse reaction involving the biomedical product. Company partners 60 (e.g., co-developers of the biomedical product) may also interface with the biomedical portal system 30.

The biomedical portal system 30 stores the collected data from the different phases in a biomedical data warehouse 44. Metadata within the biomedical data warehouse 44 describes the collected data and how it interrelates with not only data from the collected data's respective phase, but also how it relates to data collected during other phases.

Another data warehouse 46 stores genomic data, such as gene information gathered from patients tested during the clinical studies phase 36. Metadata within the genomics data warehouse 46 describes the genomic data and how it relates to biomedical product information stored within the biomedical data warehouse 44. The interrelationships between the data warehouses 44 and 46 allow genetic information to be part of the biomedical product evaluation.

For example, if several people exhibit an adverse reaction after a biomedical product has been released, then a detailed historical development profile may be constructed using the interrelationships contained within the biomedical data warehouse 44. The biomedical data warehouse's data and its interrelationships help to identify where the adverse reactions were located geographically so that demographic analysis may be performed. (Additional analysis involving the metadata may include, for example, analysis of what distributors were associated with the distribution of the biomedical product that caused the adverse reaction.) The metadata within the biomedical data warehouse 44 links the relevant product release's information with FDA approval phase information and to the other development phases' data. In this manner, the biomedical portal system 30 can identify whether such an adverse reaction was identified during the FDA approval phase 40 as well as whether the adverse reaction had been identified and studied during the discovery and clinical studies phases 34 and 36. The metadata contained within the genomic data warehouse 46 augments the detailed analysis of the adverse reaction. The genomic metadata provides genetic data that is associated with the patients tested during the clinical studies phase 36 and indicates whether the genetic data (of those patients who exhibited the adverse reaction) had a similar genetic makeup to the people in the field who also exhibited the adverse reaction.

The data warehouses 44 and 46 used to store the biomedical and genomic data and metadata may provide prediction and modeling capabilities. The data warehouses also allow for unstructured data sources 50 (e.g., data in word processing documents) to be entered as structured data (e.g., data records in a database) into the data warehouses 44 and 46. The metadata retains a record of the process involved in the unstructured data sources' conversion. Technology to build such data warehouses is available from SAS Institute Inc. located in North Carolina (which company provides such software products as Warehouse Administrator).

Users from different development phases gain access to the biomedical portal system 30 through an Internet connection 52. A server 54 receives and processes the data input and requests of the users. With respect to data input to the biomedical portal system 30, a knowledge management system 56 contains a set of graphical user interfaces tailored to obtain not only the data points associated with the particular task of a phase, but also metadata about the data points. The graphical user interfaces are constructed to capture metadata whose utility may not be fully apparent until a later development phase. For example, the FDA may be concerned with whether the biomedical product was tested under certain conditions which may not have seemed relevant during the earlier development phases. The FDA may desire testing for certain biomedical products to have been performed with patients taking Ibuprofen in addition to the biomedical product under evaluation. Also, the FDA may require that certain patient sampling sizes are needed before approval is gained. The metadata in these earlier phases may be directed to obtaining information from patients, such as whether they were taking Ibuprofen. The metadata may also provide suggestions that a larger sampling size be taken so that FDA compliance may be more easily obtained.

With respect to processing data requests of the users, an analysis and reporting module 58 uses the metadata to identify the datasets that satisfy the users' request. Another module 62 handles the more specific task of requests directed to regulatory submission and document management. Module 62 validates results for compliance with FDA requirements, such as what data conversions were performed on the data being presented to the FDA. Due to the metadata, the module 62 reduces the time for final document generations such as NDAs (New Drug Applications) and INDs (Investigational Drug Applications). It also facilitates compilation of FDA submission documents, such as ISS (Integrated Summary of Safety) and ISE (Integrated Summary of Efficacy).

Figure 2:
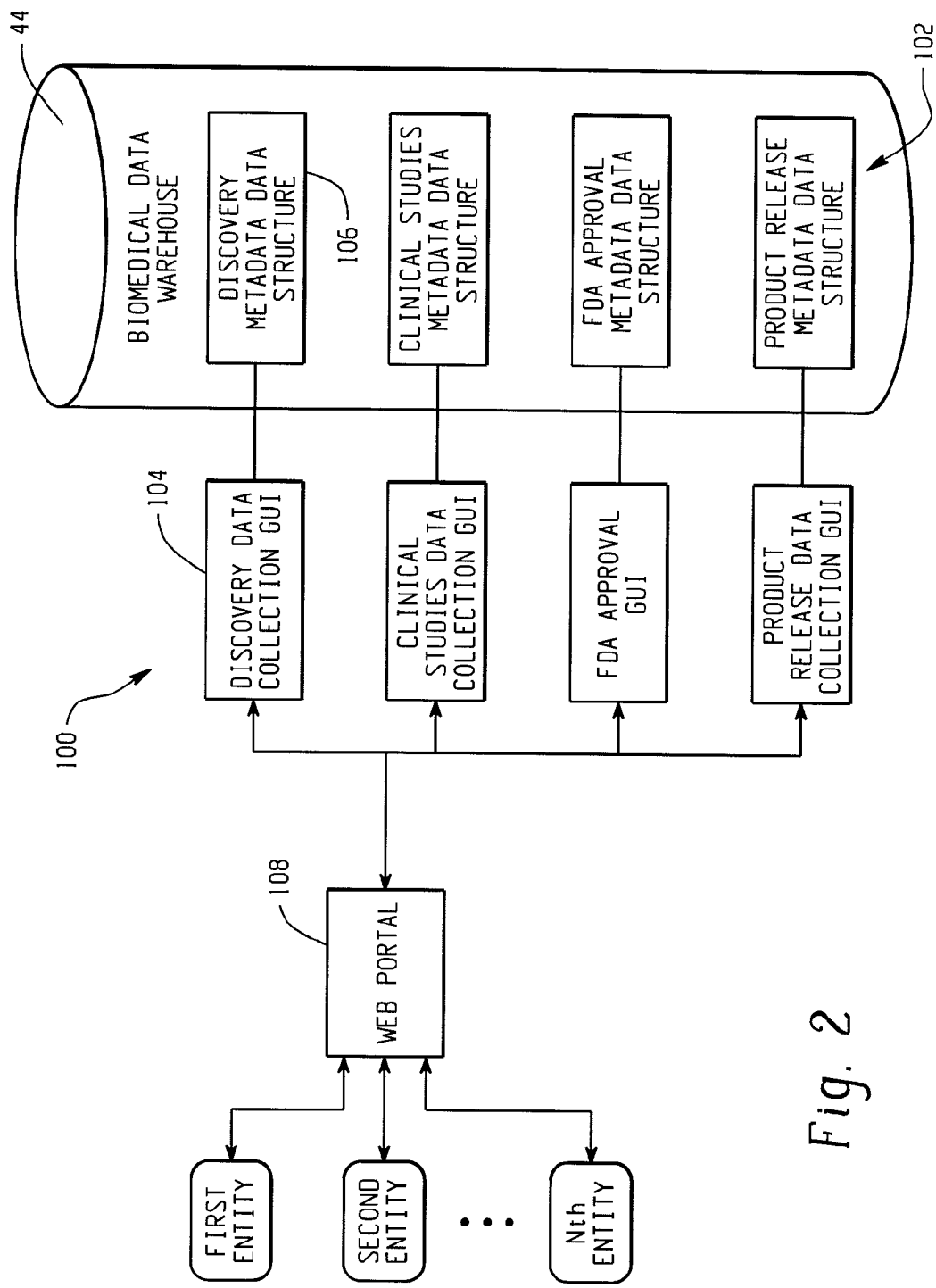
FIG. 2 is a block diagram that depicts data collection and integration across various biomedical development phases.

FIG. 2 depicts graphical user interfaces 100 (GUIs) that assist in the data collection and integration across multiple biomedical development phases. Each phase contains its own graphical user interface(s) 100 whose structures are defined by what data points are to be collected in their respective phase as well as what metadata is to be collected and stored in the metadata data structures 102. As used herein, the term graphical user interface includes using one or a series of screen interfaces to capture and display data and metadata.

Unique graphical user interfaces may be developed for each company whose biomedical development data resides within the biomedical data warehouse 44. While the appearance and certain data fields on the GUIs 100 may not be the same for each company, the GUIs 100 still capture the metadata for the development phases.

It should be understood that the data collection process may occur in many different ways. This is chiefly a result of the varied manner in which the biomedical industry acquires biomedical data. For example, the biomedical portal site 30 may collect data and metadata at approximately the same time that the data is generated. In another situation, the biomedical portal site 30 may collect data and metadata well after the data was generated. This may arise when a second company acquires rights to a biomedical product from a first company. The first company may have successfully completed the discovery phase for its biomedical product and sold the rights of the biomedical product to the second company. The second company may have purchased the rights "outright" or may have acquired the rights through acquisition of the first company. The second company uses the discovery data collection GUI 104 to "retroactively" place the discovery data and metadata into the biomedical data warehouse 44. This may be accomplished in a number of ways. For example, the second company may place unstructured discovery data into the biomedical warehouse 44 and populate the discovery metadata data structure 106 with metadata indicating the unstructured source and other attributes of the data.

FIGS. 3-13 depict graphical user interfaces associated with acquiring data and metadata. The biomedical portal site uses metadata to drive its component applications. Specifically, the clinical metadata is used by a data explorer and a reporting wizard as shown in the following examples. Metadata is captured dynamically from the user as shown in FIGS. 3-5. At the protocol level as shown in FIG. 3, the metadata describes (among other things) the patient identifier information 150, the visit identifier information 152 and the study period information 154. At the dataset level as shown in FIG. 4, the metadata describes the variables (fields) within the dataset in terms of variable names, descriptions, type, length, format and informat, as well as data key information (shown at reference numeral 180). Additionally as shown in FIG. 5, measure definition and grouping metadata (190 and 192) is captured for further use by the data explorer.

The data explorer reads the metadata that describes the protocol and datasets to dynamically build a domain and measures tree. This tree 200, which is rendered as a Windows-like folder tree, appears on the left-hand side of FIGS. 6-10B. As the metadata from FIGS. 3-5 is updated, the resulting changes are rendered in the data explorer tree 200 of FIGS. 6-10B.

Figure 6:
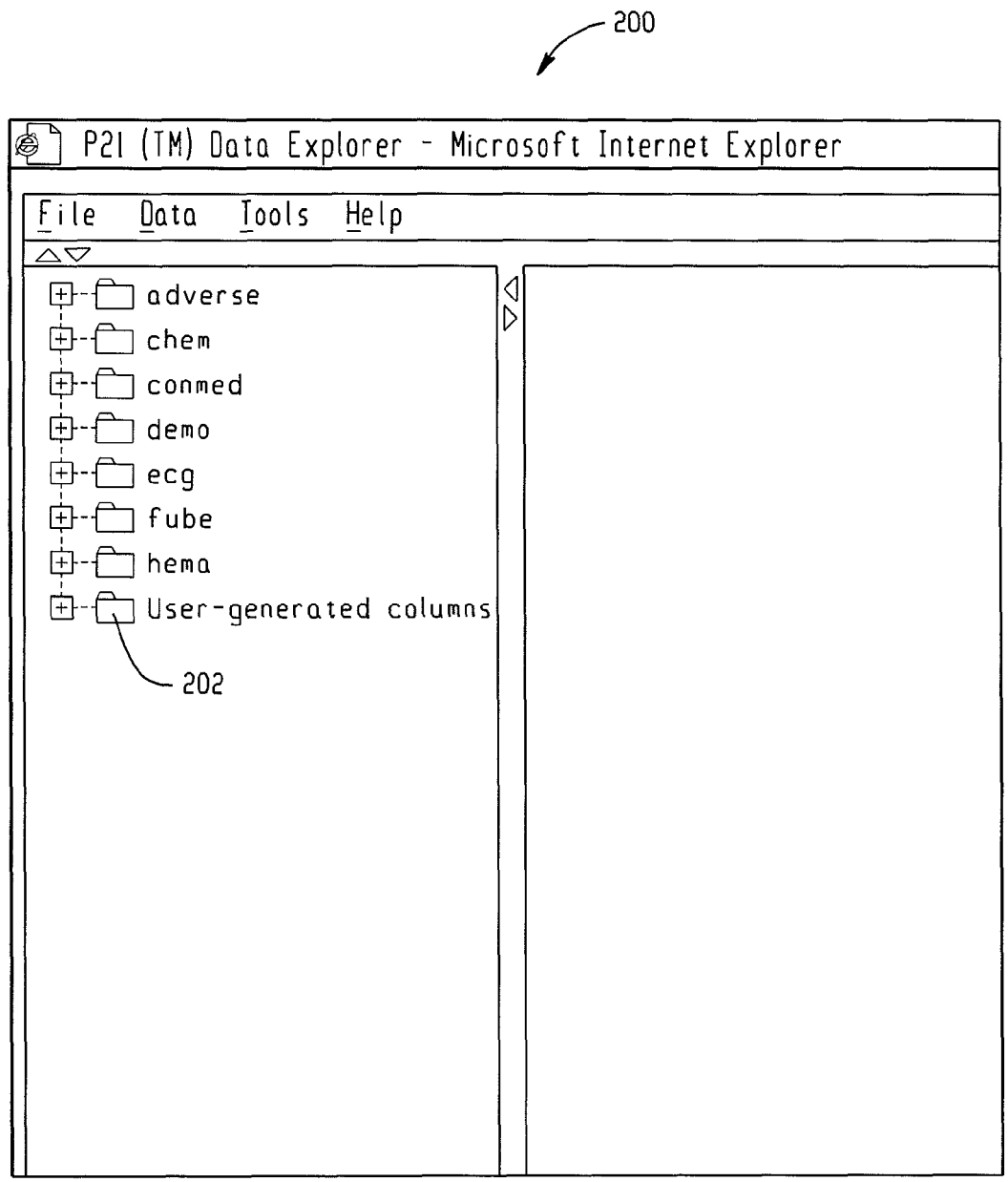

When the data explorer is started, the initial view (as shown in FIG. 6) renders only the datasets available for a particular protocol as defined in the platform metadata, as well as a new data table labeled User-generated columns 202.

Figure 7:
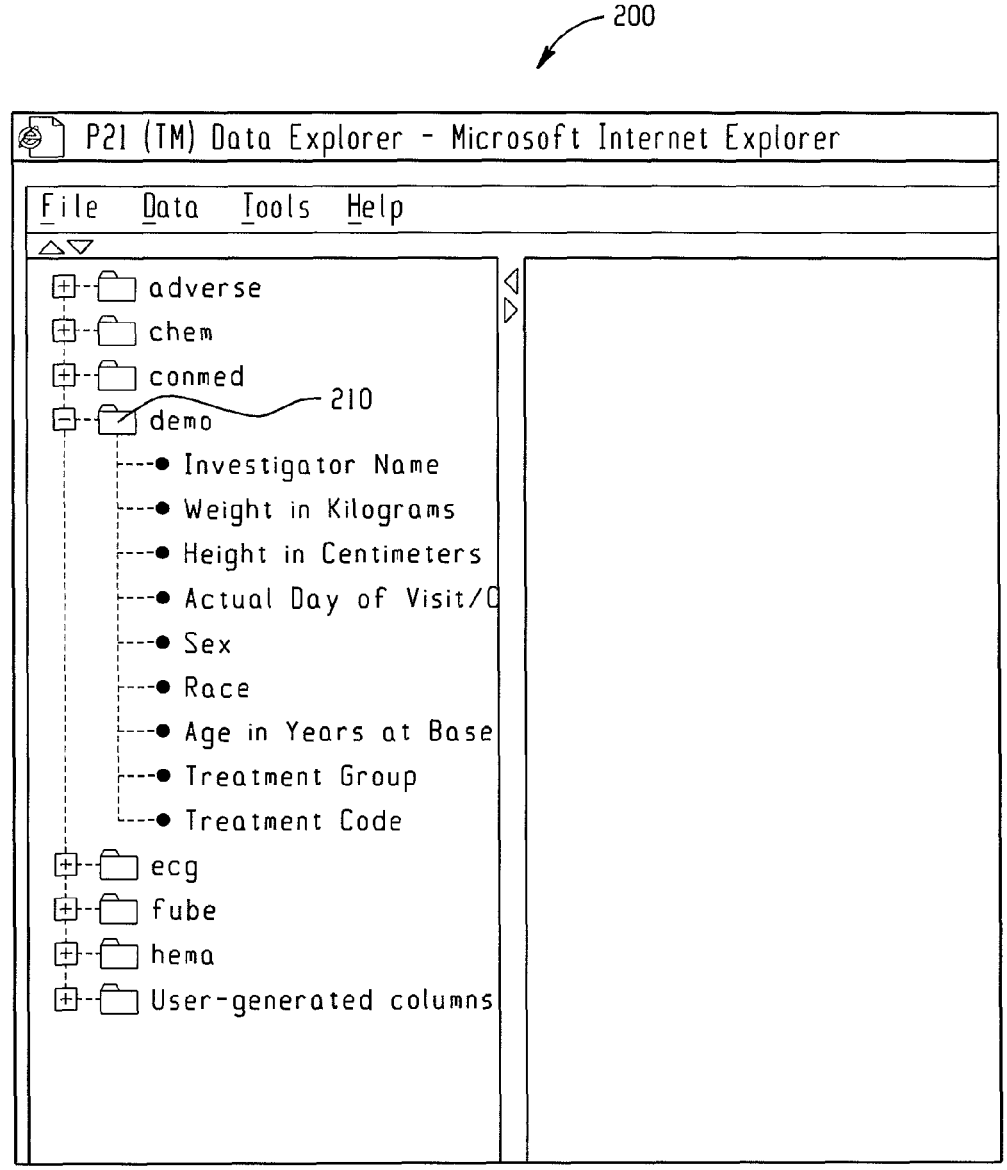
Figure 8:
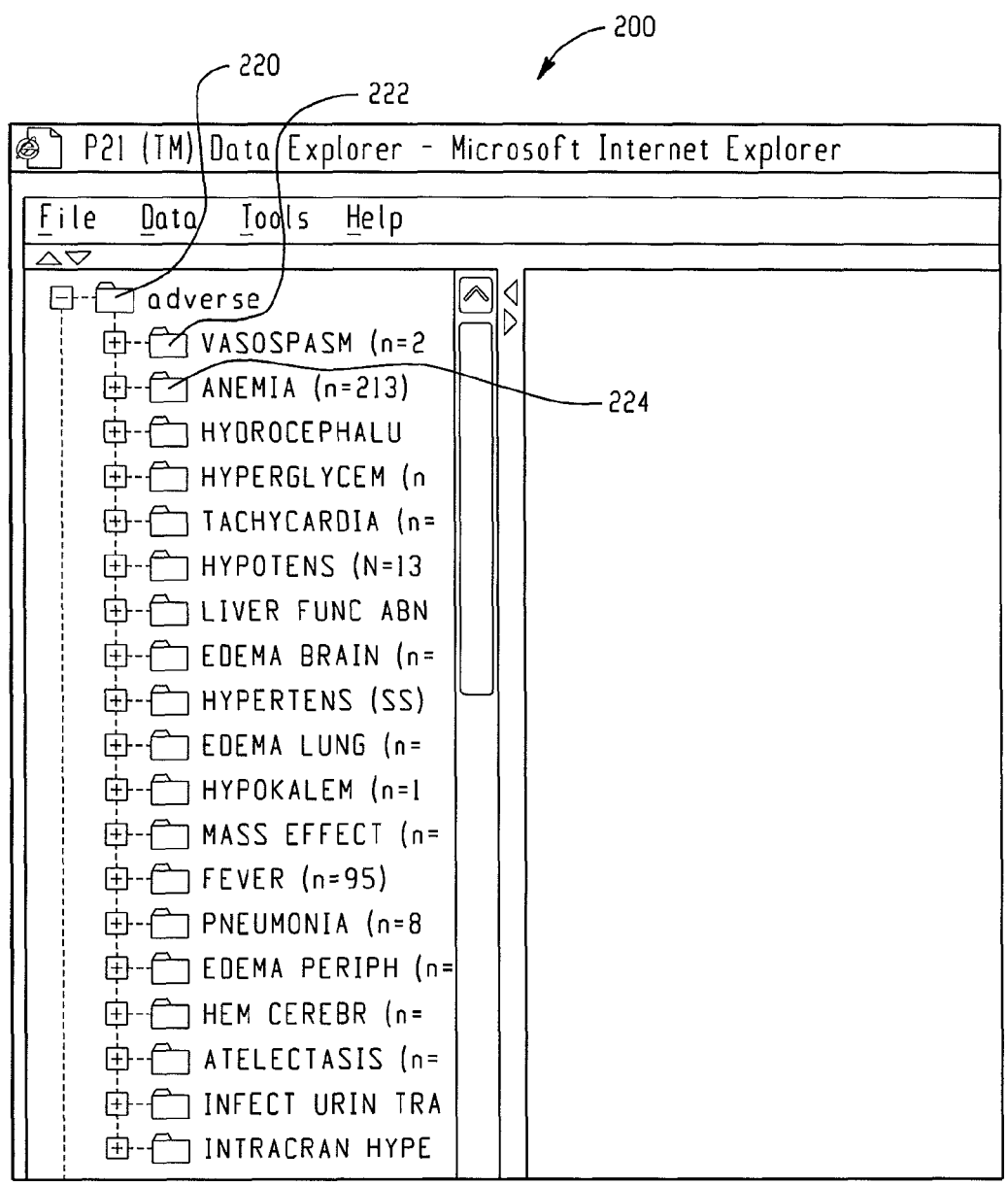

As the folders are expanded, the metadata that describes each dataset is rendered as shown in FIGS. 7 and 8. FIG. 7 indicates the variables (measures) available for review within the demography dataset 210. These lists of variables are dynamically created from the metadata that describes each dataset.

In FIG. 8, the adverse events domain 220 has been expanded. The measures that are rendered are again built dynamically, based upon the metadata that describes the adverse events. In this case, the measure definitions and groupings (shown in FIG. 5) are used to dynamically structure the domains/measures tree. The measures vasospasm 222, anemia 224, etc., are not present in the adverse events dataset as individual variables, but are rendered based upon the dataset metadata.

Figure 9:
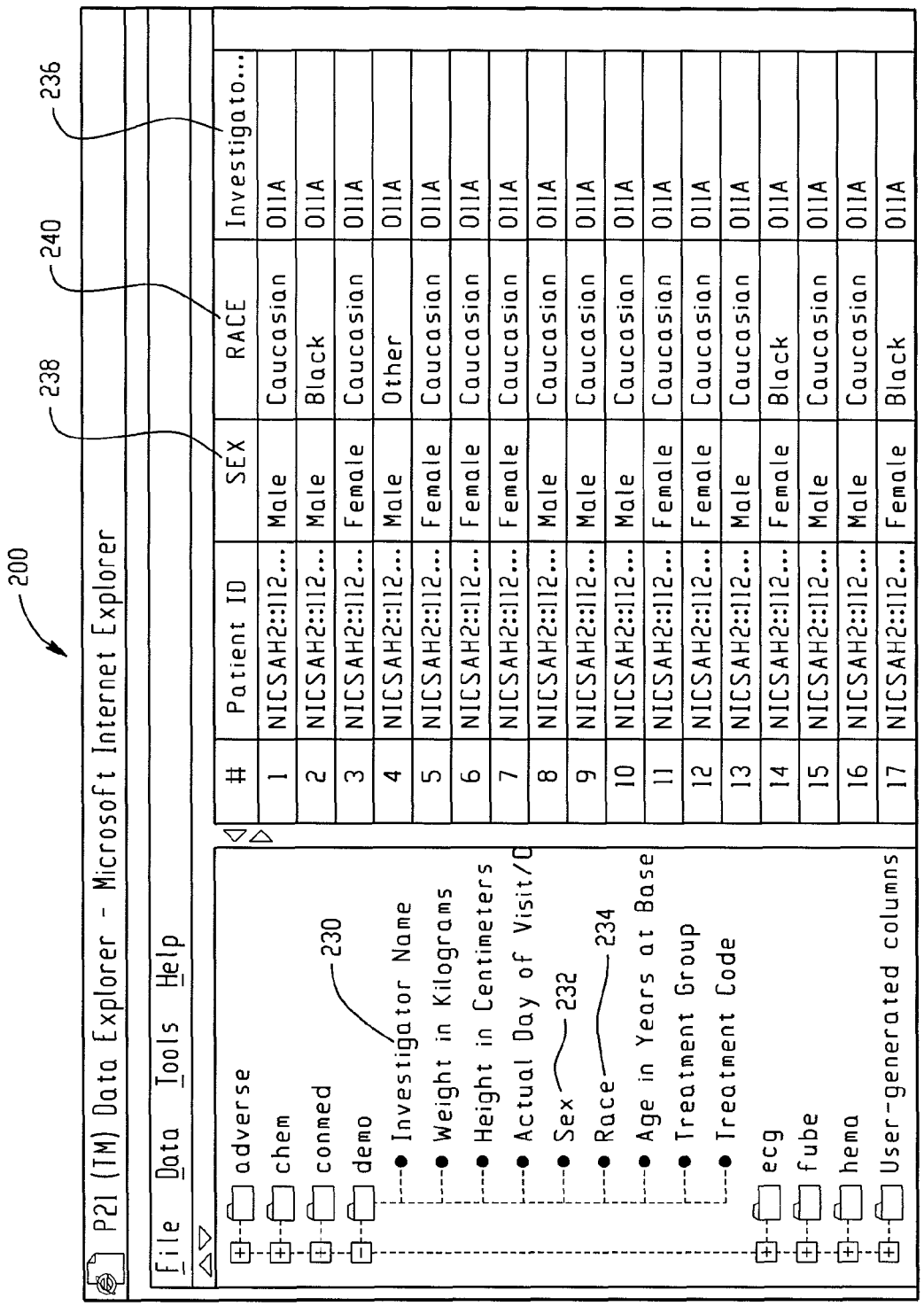
Figure 10A:
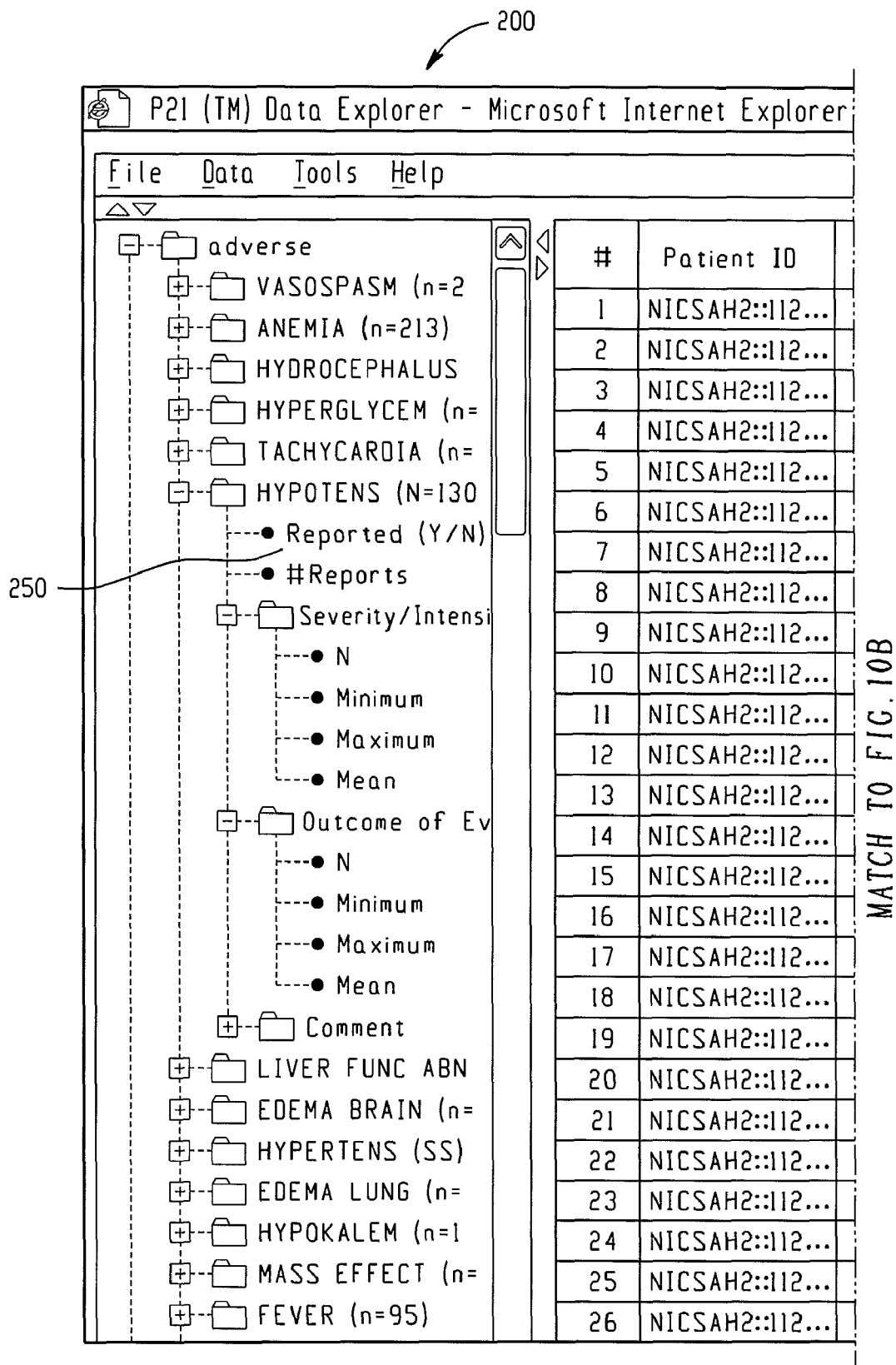
Figure 10B:
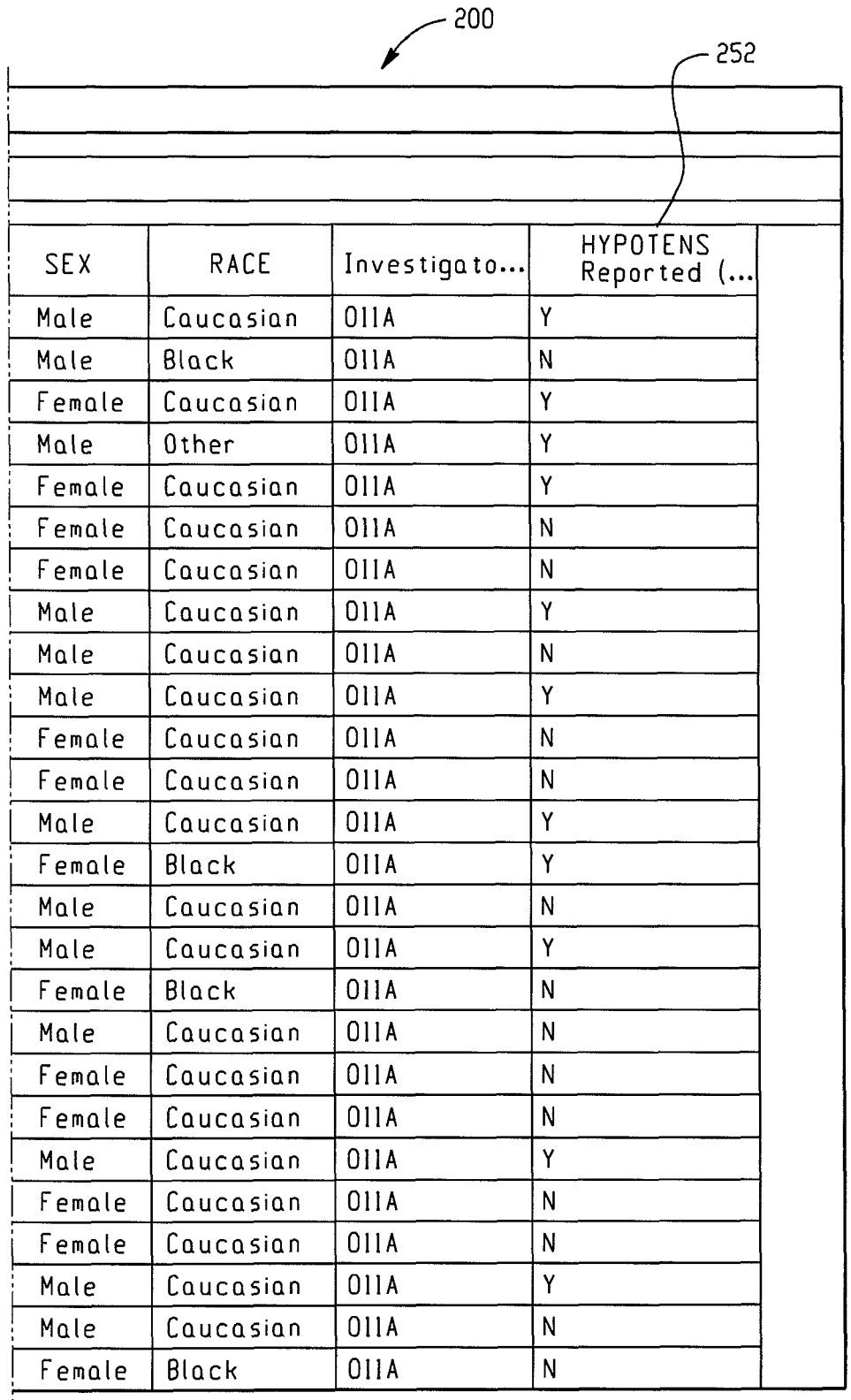

As measures are selected as shown in FIGS. 9, 10A, and 10B, the selected information is used to dynamically render a viewable table (as shown in the right-hand side of the data explorer window). The data being displayed in this window may not exist as shown anywhere in the database. Instead, the metadata that describes the protocol and datasets is used to merge (join) the selected datasets, and to display the individual variables as described by the dataset metadata—both in terms of variable descriptors as well as measure definitions and groupings. FIG. 9 shows the viewing of the data associated with the demography domain (the investigator name 230, sex 232, and race 234 have been selected and their data is shown respectively in columns 236, 238, and 240). FIGS. 10A and 10B show the viewing of the data associated with the demography and adverse events domain (Hypotens reported 250 has been selected and is viewed in column 252).

Figure 11:
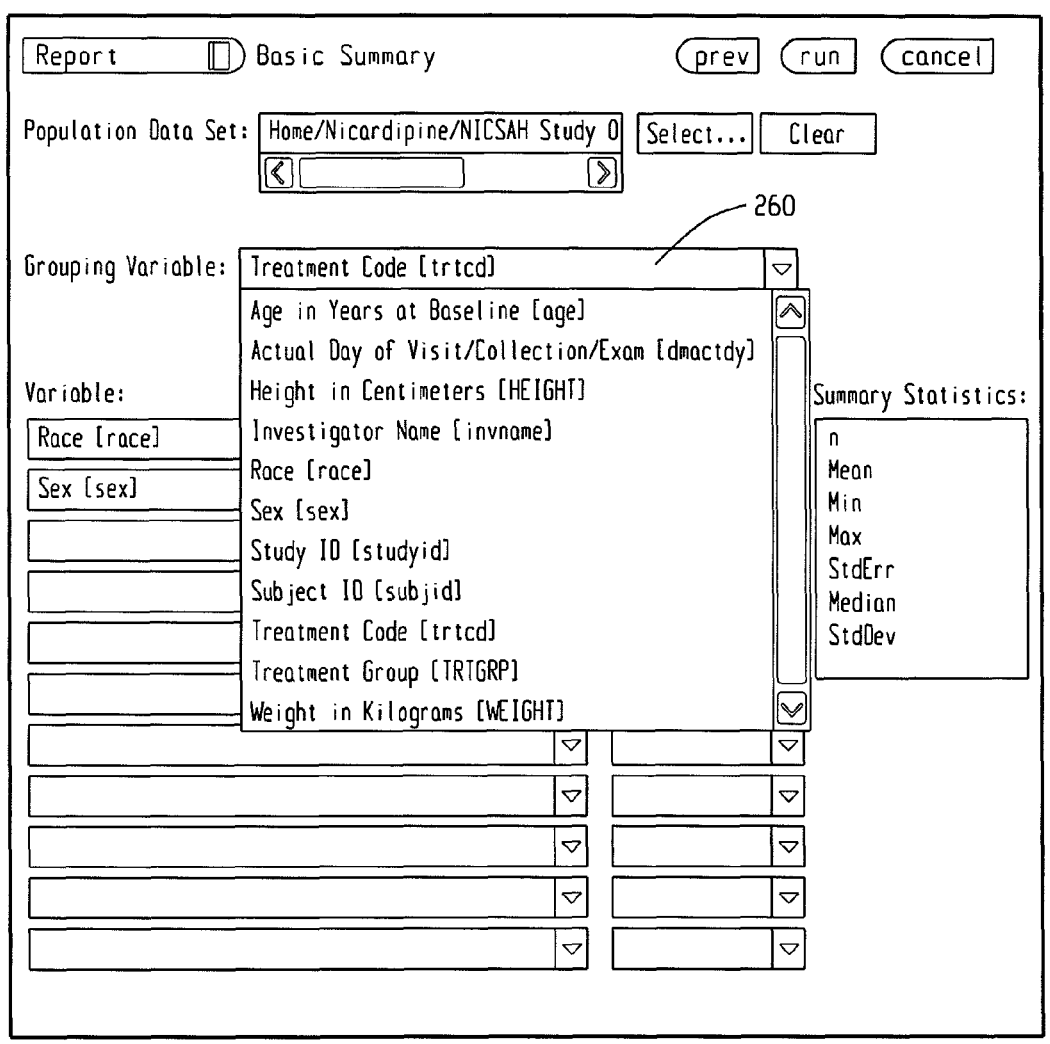
Figure 12:

Metadata is also used to drive the reporting wizard as shown in FIGS. 11 and 12. In this wizard, user-specified parameters are used to create statistical and listing summary reports of the clinical data. Both the wizard interface as well as the report output are controlled by the available metadata. FIGS. 11 and 12 show how the metadata is used to control the variable selection process for the statistical analysis variables. In this example, only variables described by the metadata for the demography dataset are available for selection. The labels associated with these variables are defined within the dataset metadata. FIG. 11 depicts the dynamic selection of grouping variable (as shown by reference numeral 260), and FIG. 12 depicts the dynamic selection of statistical variables (as shown at reference numeral 270).

In FIG. 13, the results of applying the statistical analysis to the selected variables are displayed to form a demography statistical report 280. The metadata that describes the individual data sets has been used to label the results sections (Treatment Code 282, Race 284, etc.). As discussed earlier, updating this metadata subsequently results in updating the report output.

It must be understood that the use of metadata by the biomedical site portal is not limited to only the data explorer and the reporting wizard, although it is most visible to the user in these applications, but is used in throughout in other data collection, analysis and reporting operations as described herein.

Figure 14:
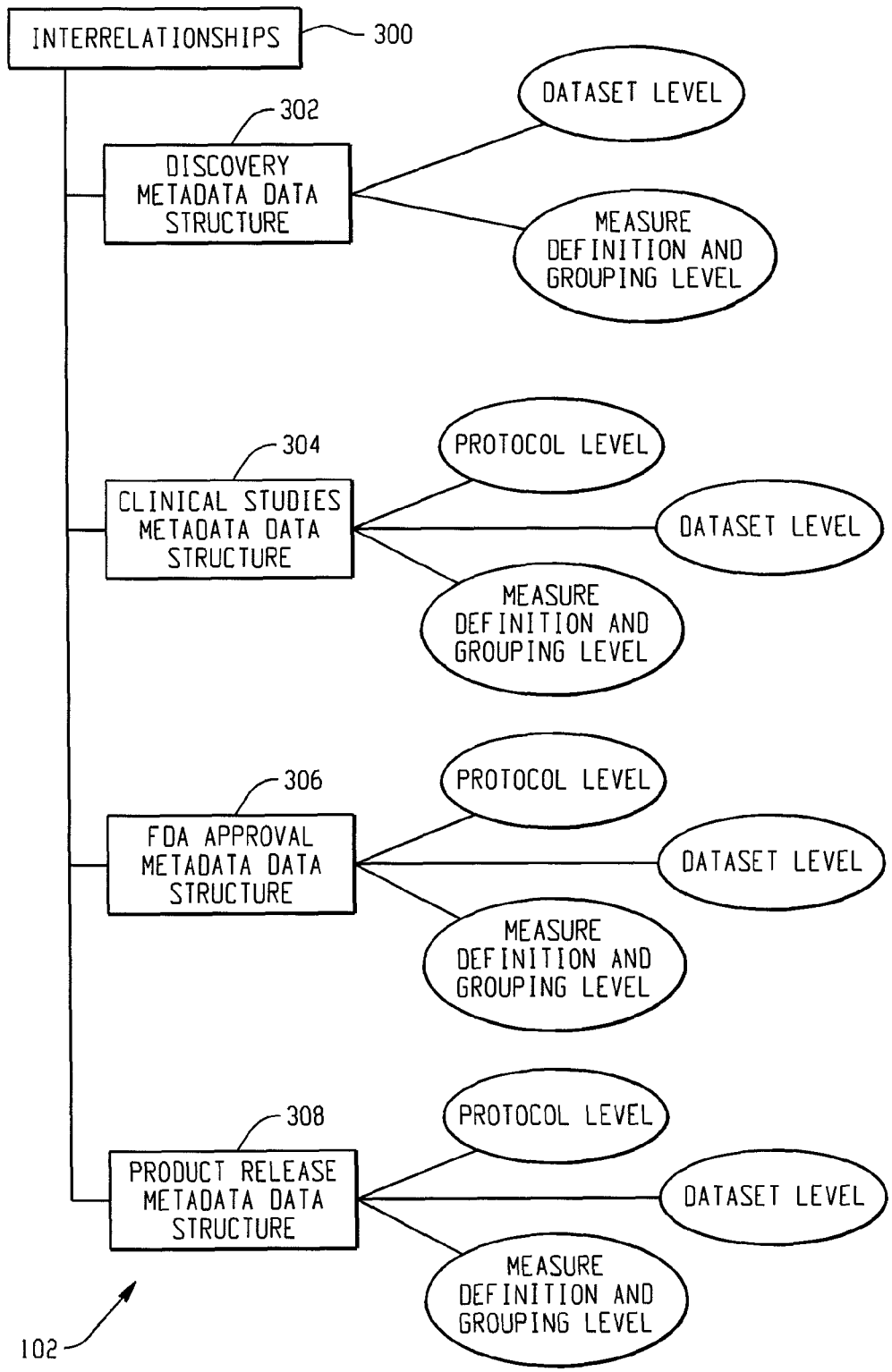
FIG. 14 is a data structure diagram that depicts the interrelationships among the different phases' metadata structure.

FIG. 14 depicts the interrelationships 300 among the different phases' metadata structure. The interrelationships 300 permit traceability among the different phases. FDA audit trails and adverse effect analysis are but a few of the uses for the traceability feature. The interrelationships 300 may interrelate not only on an "intra-developmental" phase level, but also on an "inter-developmental" phase level. Metadata may be used to describe the interrelationships to allow analysts to exploit the interrelationships. Especially, when personnel change jobs and companies, this type of knowledge retention in the form of interrelationship metadata is valuable.

The discovery metadata data structure 302 includes metadata at the dataset level and the measure definition and grouping level. The metadata data structures 304, 306, and 308 include metadata at the protocol level, dataset level, and the measure definition and grouping level. It should be understood that additional levels may be added to the metadata data structures in order to collect the metadata that best fits the situation at hand.

Figure 15:
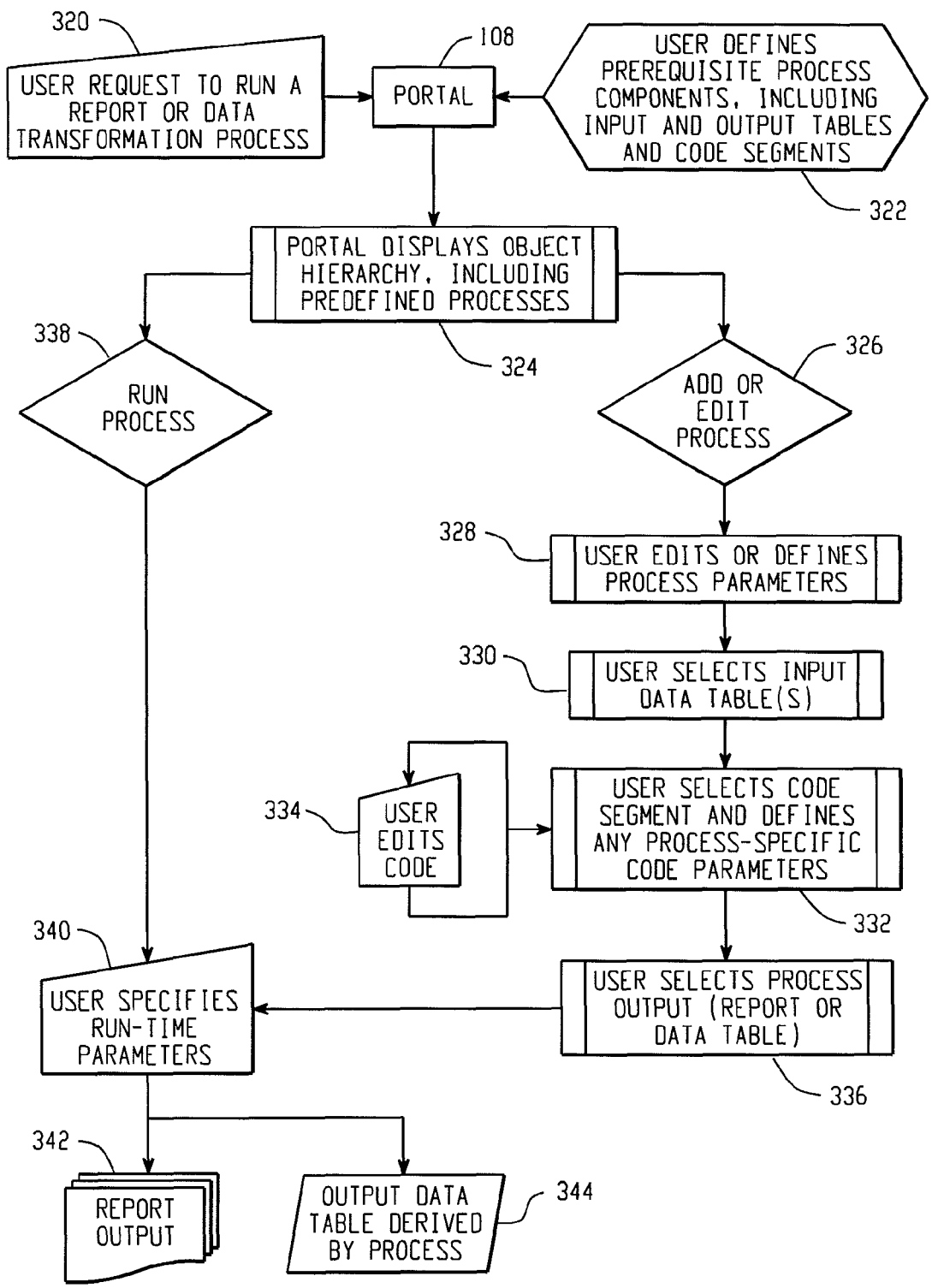
FIG. 15 is a flowchart that depicts analysis and reporting processes for a biomedical portal site.

FIG. 15 depicts a flowchart of the analysis and reporting processes for the biomedical portal site. At input block 320, a user requests to run a report or data transformation process. The user's request is funneled to the portal 108. The user further provides to the portal 108 prerequisite process components such as input and output tables and code segments at step 322. Within the field of the invention, code segments refer to units of program code which are assembled to specify how a report is to be generated.

With the user input data defined, the portal 108 displays at block 324 the object hierarchy, including predefined processes. At this processing point, the user may add/edit the process at 326 or may run the reporting process at 338 that will generate the desired report. If the user decides to add/edit the process at 326, then processing continues at block 328. At block 328, the user edits or defines process parameters and then at block 330 the user selects the input data tables to be used in the report. Next at block 332, the user selects the code segments and defines any process-specific code parameters, such as specifying that only a terse summary report be generated instead of a verbose report. As shown by the iterative loop 334, the user may edit the code as necessary in order to adequately define the report data and format. The user at block 336 selects the process output which may be a report or a data table.

After the user has completed the add/edit process or after the user has run the reporting process, the user specifies the run-time report parameters at input block 340. Based upon what report format the user has selected to view the results, the user receives either the results as report output 342 or as output data table 344. The reporting process is repeated as necessary by the user.

Figure 16:
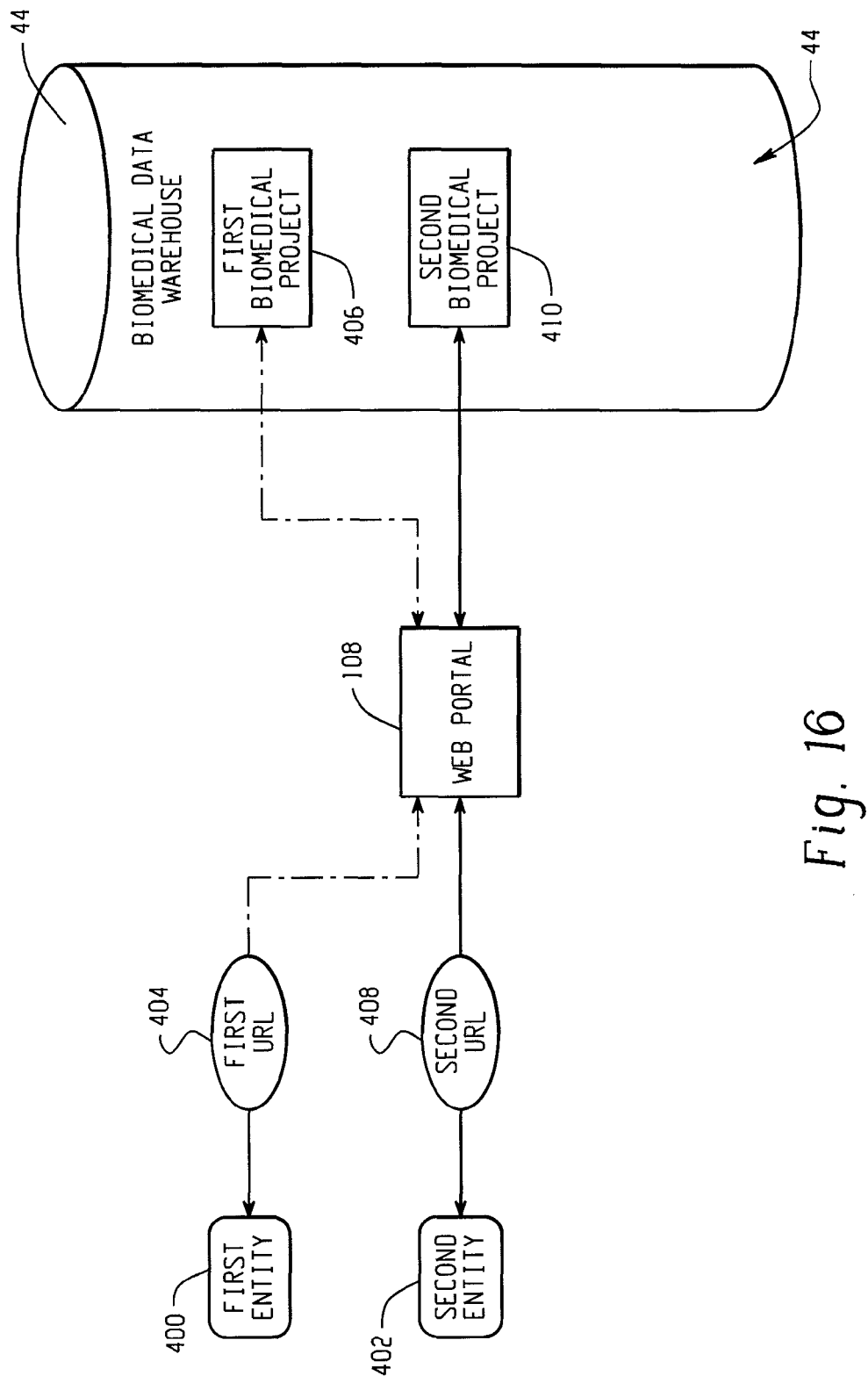
FIGS. 16-18 are block diagrams that depict a project data access and ownership transfer scheme used within a biomedical portal site.
Figure 17:
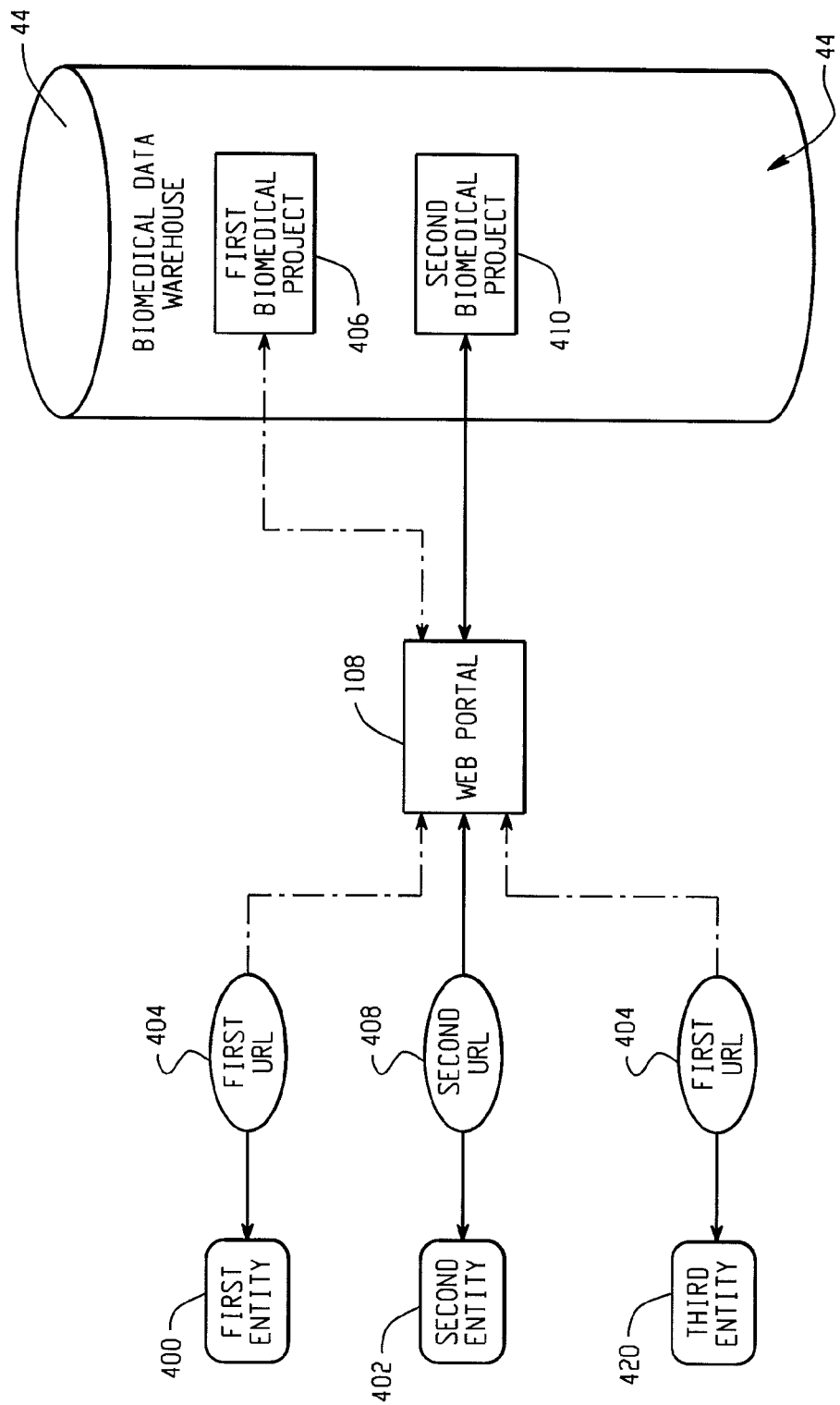
Figure 18:
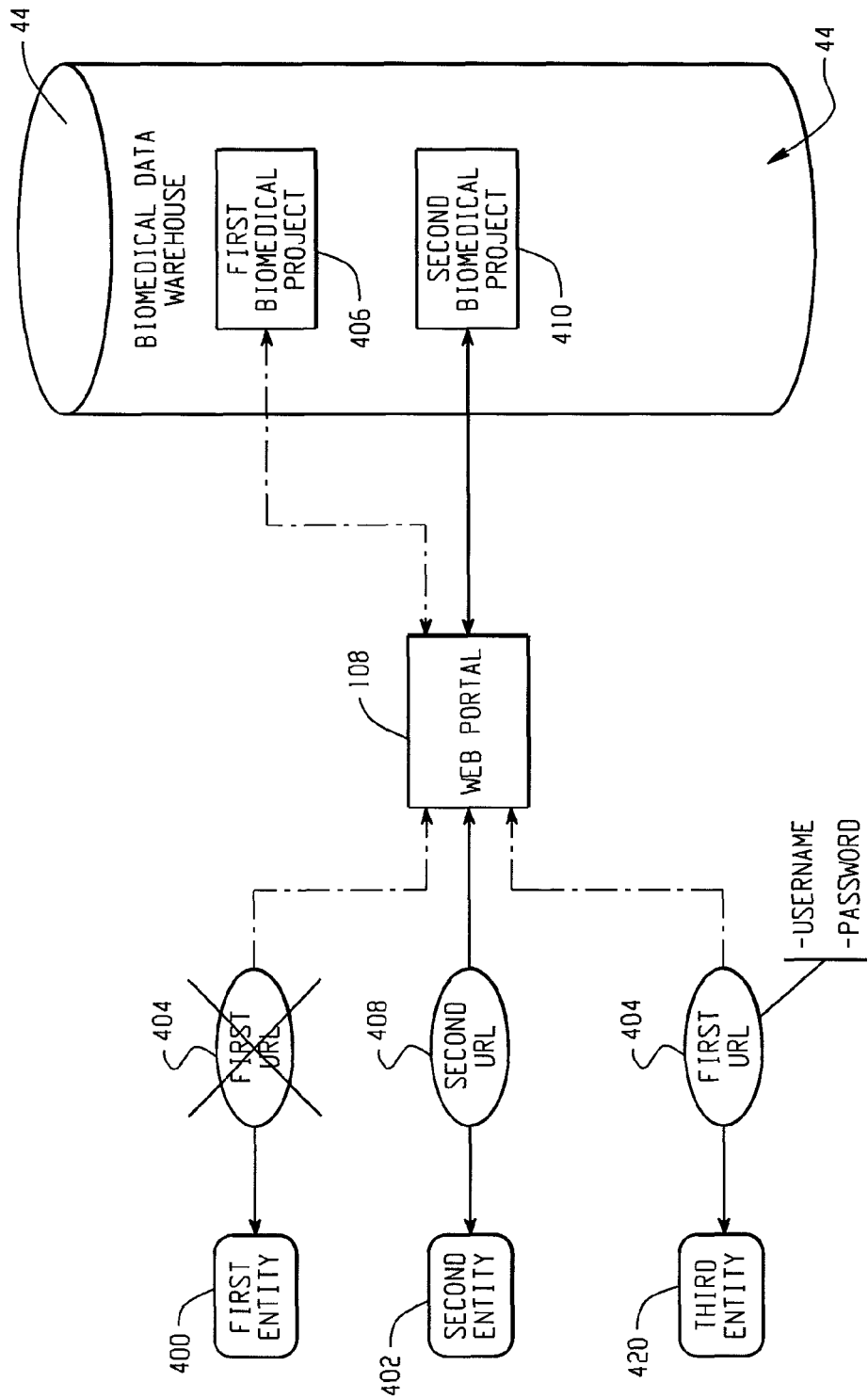

FIGS. 16-18 depict a project data access and ownership transfer scheme used within the biomedical portal site. In the example of FIGS. 16-18, two different entities 400 and 402 store their data within the biomedical data warehouse 44 that is maintained by a third party. This arrangement may arise in an Application Service Provider (ASP) situation. The first entity 400 is provided with a first uniform resource locator 404 (URL) that provides access only to the first company's biomedical project 406. The second entity 402 is provided with a second uniform resource locator 408 (URL) that provides access only to the second company's biomedical project 410. Security may be supplemented by associating user names and passwords with the URLs 404 and 408. It must be understood that the entities referred herein may include many different entities so as to parallel how the biomedical and pharmaceutical industries operate. For example, the first and second entities may be different companies; or the first and second entities may be different divisions within the same division but responsible for different development phases; etc.

With reference to FIG. 17, a third entity 420 is allowed in this example access to the first company's biomedical project 406. The third entity 420 may be another company that is interested in acquiring the rights to the first biomedical project 406, or the third entity 400 may have formed a joint venture with the first company to assist the first company in further developing the first biomedical project 406. The third entity 420 may also be the FDA who is allowed access to the first biomedical project 406 in order to evaluate the first biomedical project 406 for approval.

The third entity 420 is provided with the first URL 404 as well as a user name and password that may be the same as that used by the first entity 400. However, different user names and passwords may be provided to the third entity 400 in order to grant security access to only a subset of the data and metadata contained within the first biomedical project 406.

FIG. 18 represents the efficient manner in which ownership to a biomedical project is transferred between entities. In this exemplary situation of FIG. 18, the third entity has purchased the rights to the first biomedical project 406 and under the terms of the purchase the first entity 400 is not allowed to further develop the project 406 nor have access to the project 406. To accomplish the ownership change, the third entity 420 is provided with the first URL 404, but with a different user name and password, thereby precluding the first entity 400 from accessing the first biomedical project. It must be understood that additional security mechanisms may be used to further prevent access by the first entity 400 of the project 406.

Figure 19:
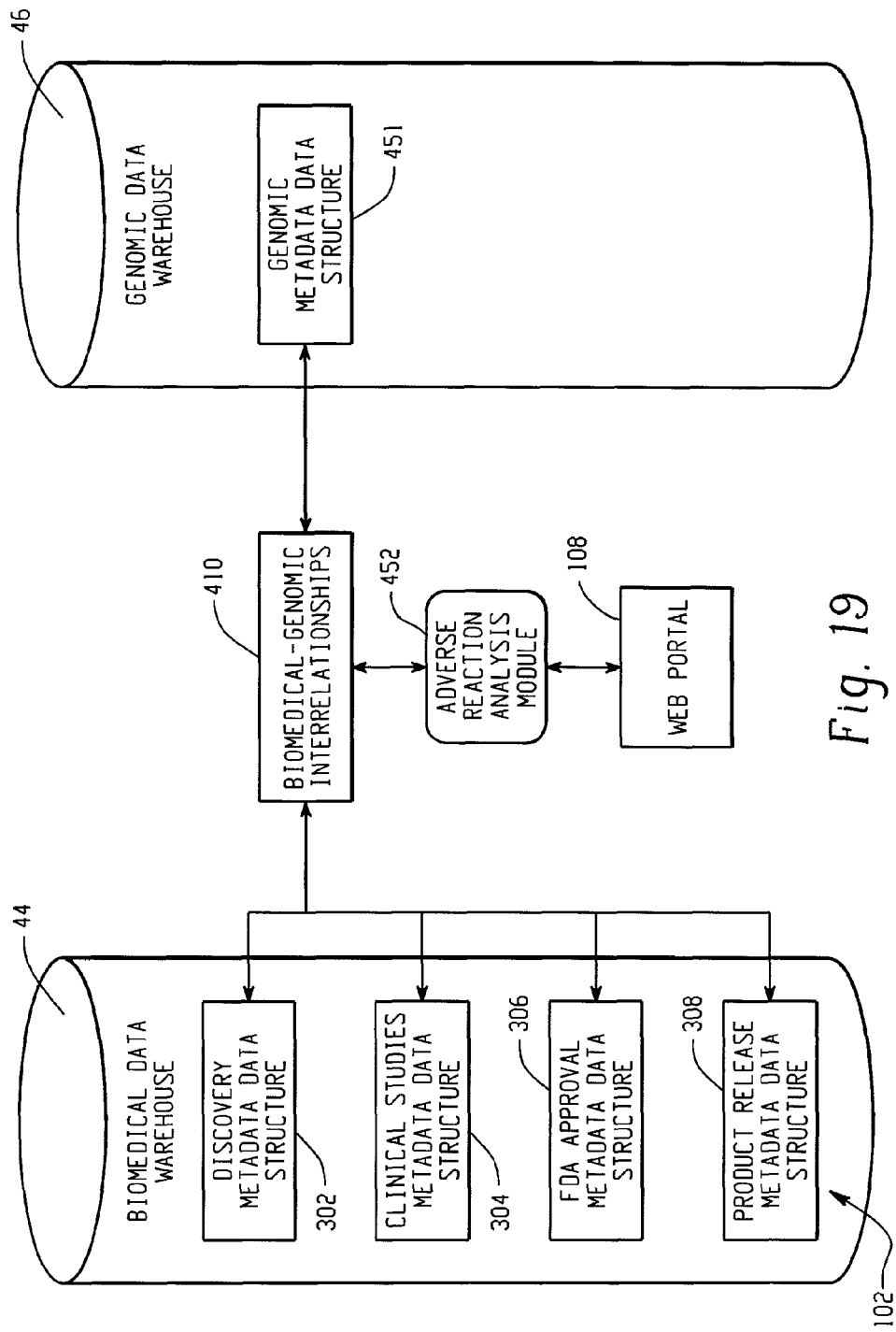
FIG. 19 is a block diagram that depicts an interrelationship scheme between the biomedical data warehouse and the genomic data warehouse.

FIG. 19 depicts an interrelationship scheme between the biomedical data warehouse 44 and the genomic data warehouse 46. Both data warehouses 44 and 46 contain metadata which describe their respective internal data. Moreover, biomedical-genomic interrelationships 450 exist to link data contained in the two data warehouses 44 and 46. For example, a patient's clinical data gathered during the clinical studies phase may be linked through the interrelationships 450 to the patient's genomic information and the metadata contained in the genomic metadata data structure 451.

The linkages 450 prove valuable in such analysis as may be performed by an adverse reaction analysis module 452. The adverse reaction analysis module 452 may be investigating whether adverse reactions (discovered after release of a biomedical product) had been identified and studied during an earlier phase (such as the clinical studies phase). If it had not been identified, then the adverse reaction analysis module 452 provides suggestions on what changes (especially in the metadata collection) should occur so that future tests which involve this or similar types of biomedical products may more likely identify the adverse reaction. If the adverse reaction had been identified and studied in the clinical phase, then the genetic makeup of the clinical patients may be compared to the genetic makeup of the post-release adversely affected people to achieve a better solution.

Figure 20:
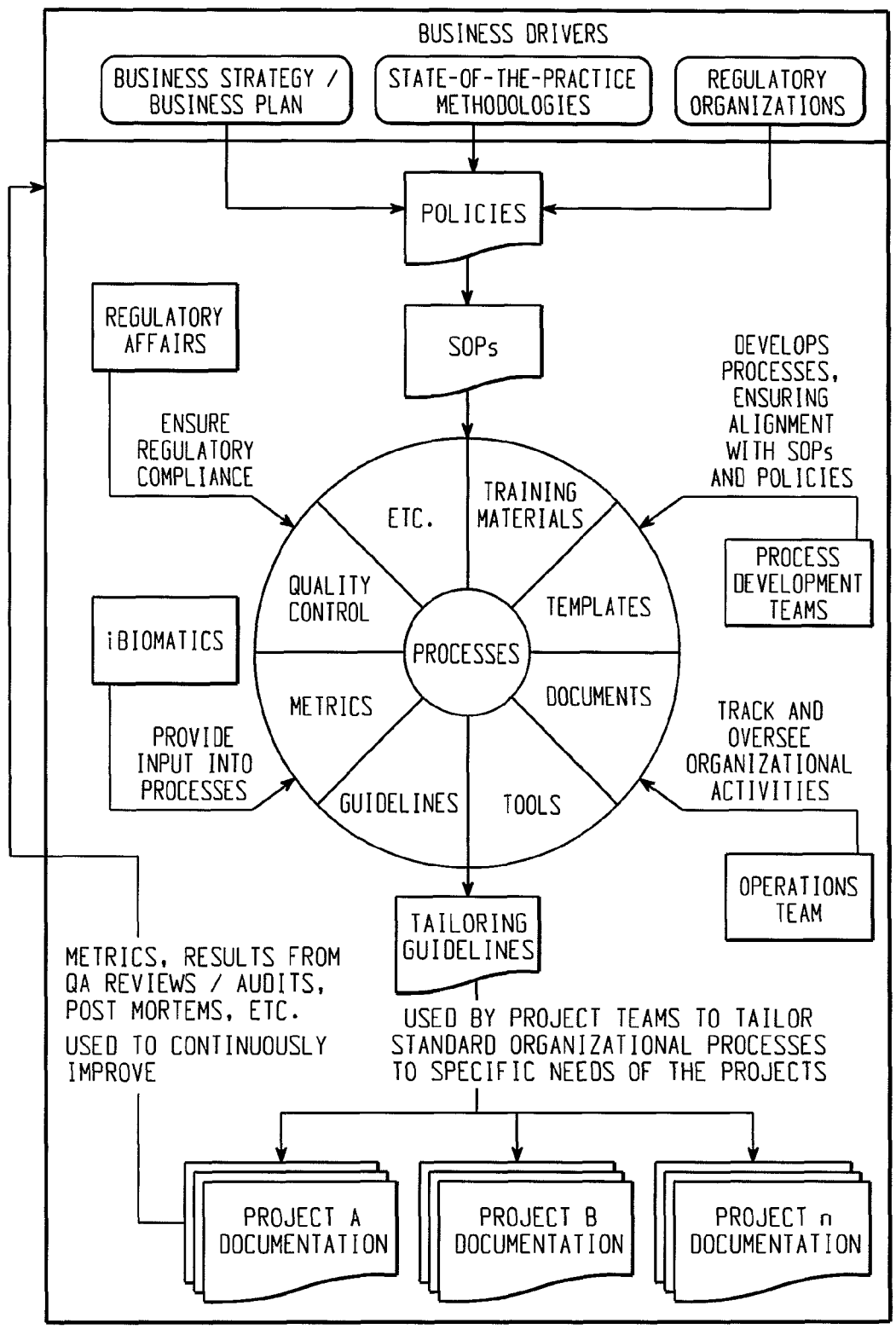
FIG. 20 is a block diagram that depicts the effectiveness of a biomedical portal site to accomplish quality management within an FDA compliant environment.

FIG. 20 depicts the effectiveness of the biomedical portal site to accomplish quality management within an FDA compliant environment. The biomedical portal site comports with current good clinical, manufacturing and laboratory practices and regulations such as 21 CFR Part 11 (electronic records; electronic signatures) which mandate that computerized systems used to create, modify, maintain, archive, retrieve or transmit electronic records shall be validated to ensure accuracy, reliability, and consistent intended performance. The biomedical web portal ensures that there is validation according to these regulations and industry practices. The biomedical portal site contains a framework of policies, standard operating procedures (SOPs), processes, enabling tools, tailoring guidelines and an internal infrastructure that collectively prescribe, govern, and guide subsequent biomedical portal development.

Business drivers that impact the biomedical web portal include business strategy, state-of-the-practice methodologies and regulations. The overall business strategy and vision are defined based on input from biomedical management. Current state-of-the-practice methodologies are derived from the pharmaceutical, biotechnology, and software engineering industries. Best practices are adopted from the Capability Maturity Model (CMM) for Software developed by the Software Engineering Institute of Carnegie Mellon University. Regulations that affect business include 21 CFR Part 11 (Electronic Records; Electronic Signatures).

Policies provide the rules that govern, guide, or constrain operations in the biomedical project's organization. They reflect that actions are to be taken to ensure that processes are established to define operations and that the processes will endure. Business strategy, state-of-the-practice methodologies and regulations contribute to the policies.

Regulatory organizations require that SOPs be in place in organizations that serve the pharmaceutical and biotechnological industry. General SOP definitions share the following characteristics:

SOPs are written instructions that identify satisfactory methods to ensure the quality and integrity of, among other things, data generated in the course of a study.

Deviations to SOPs must be reported, recorded and responded to in an authorized fashion.

Changes to SOPs must be made in authorized fashion.

SOPs serve as regulatory checkpoints for the biomedical project's organization. They describe the tasks that must be performed in order to be compliant with FDA regulations. Further, their development, implementation and maintenance are performed in a manner that is consistent with regulations.

Processes describe operations (i.e., what the biomedical project organization does) and detail the sequence of steps performed for a given purpose (i.e., how the biomedical project organization does it). The processes are supported by a methodology we refer to as whole product wheel elements that are shown in FIG. 20. These elements are enabling tools and methods that ensure the adoption of the processes across the organization. Examples of these elements are training, tools, metrics, and installation support.

Processes ensure that products are developed and maintained using a well-defined system development life cycle that is consistent with current guidance documents. Detailed requirements specifications are developed and analyzed to lay the foundation for development activities. Planning methods are used to plan validation and development activities, identifying potential risks and determining actions to mitigate these risks. Project management and quality assurance are in place to track the progress and quality of the system and to take corrective actions when actual results deviate from planned results. Established development methods are used to build the system. These methods have quality control activities built into the processes to ensure that quality is built in, not added on to the end. Before movement of the system to production, a number of assessments are performed to ensure a valid environment according to regulations and engineering practices. These activities include user training, installation qualification/operational qualification (IQ/OQ) testing, and user acceptance testing. The system is placed under change control to ensure ongoing validation throughout the life cycle of the system.

In most cases, general SOPs and processes apply to all areas of the organization. Where differences in projects and customers exist that cannot be accommodated within the existing procedural structure, tailoring guidelines are established to provide a version of the process for specific types of projects. The quality lead person on each project works with the project team to tailor the standard processes according to the documented guidelines for the specific needs of the project.

In order for the quality management system to work efficiently and effectively, a balance is achieved among the various components. This balance is achieved through the collaborative efforts of the regulatory affairs, software process engineering and quality management systems departments. The quality management systems department supports the establishment, monitoring and continuous improvement of the quality system. Regulatory affairs ensure the internal regulatory compliance of the biomedical portal site. Process Engineering is responsible for managing the effort of developing and improving software engineering processes that support policies and SOPs.

The preferred embodiment described with reference to the drawing figures is presented only to demonstrate an example of the invention. Additional, and/or alternative, embodiments of the invention would be apparent to one of ordinary skill in the art upon reading this disclosure. For example, the biomedical portal site may assume many different configurations. A configuration may include each entity (e.g., company) having its own web portal to its own server and its own data warehouse. Another configuration may include two entities accessing data warehouses through the same web portal but their respective projects are contained in separate data warehouses.

The invention claimed is:

1. A computer-implemented method for integrating biomedical development information, comprising:
    receiving, using one or more processors, biomedical development data from each of a plurality of biomedical development phases;
    receiving, using the one or more processors, metadata from each of the plurality of biomedical development phases relating to the received biomedical development data;
    storing, using the one or more processors, the received metadata in a database using a plurality of metadata structures, each of the plurality of metadata structures being specific to a different one of the plurality of biomedical development phases;
    processing, using the one or more processors, the metadata to generate links between two or more of the plurality of metadata structures to identify how biomedical development data received during one biomedical development phase interrelates with other biomedical development data received during another biomedical development phase;
    identifying an adverse reaction; and
    determining, using the one or more processors, whether the identified adverse reaction had been previously identified, wherein determining includes using one or more of the generated links, and wherein when the identified adverse reaction has not been previously identified, one or more recommendations for receiving metadata are generated to improve the likelihood of identifying any future adverse reactions.

2. The computer-implemented method of claim 1, further comprising:
    processing, using the one or more processors, the biomedical development data and the metadata to generate a record of the biomedical development process for submission to the United States Food and Drug Administration (FDA).

3. The computer-implemented method of claim 1, further comprising:
    processing, using the one or more processors, the metadata to generate links within the same metadata structure to identify interrelationships between biomedical development data received during the same biomedical development phase.

4. The computer-implemented method of claim 1, wherein the biomedical development data is received using one or more graphical interfaces, and wherein the one or more graphical interfaces include a product release graphical interface specific to a product release phase of the biomedical development process.

5. The computer-implemented method of claim 4, wherein the one or more graphical interfaces include an adverse reaction graphical interface that is configured to receive data that identifies information relating to adverse reactions in patients, and wherein information received by the adverse reaction graphical interface is used to identify interrelationships among adverse reactions in different patients.

6. The computer-implemented method of claim 4, wherein the one or more graphical interfaces include an FDA approval graphical interface specific to an FDA approval phase of the biomedical development process.

7. The computer-implemented method of claim 6, wherein the FDA approval graphical interface is configured to receive data corresponding to one or more areas of concern identified by the FDA.

8. The computer-implemented method of claim 4, wherein the one or more graphical interfaces include a discovery phase graphical interface specific to a discovery phase of the biomedical development process.

9. The computer-implemented method of claim 8, wherein the discovery phase graphical interface is configured to receive data that identifies how often test measurements were obtained during the discovery phase and any units associated with the test measurements.

10. The computer-implemented method of claim 9, wherein one or more interrelationships between the test measurements obtained during the discovery phase are identified.

11. The computer-implemented method of claim 8, wherein the discovery phase graphical interface is configured to receive data that specifies one or more data manipulations performed upon biomedical development data collected during the discovery phase.

12. The computer-implemented method of claim 11, wherein one or more interrelationships between the one or more data manipulations performed during the discovery phase are identified.

13. A system, comprising:
    one or more processors;
    a computer-readable storage medium containing instructions configured to cause the one or more processors to perform operations, including:
    receiving biomedical development data from each of a plurality of biomedical development phases;

receiving metadata from each of the plurality of biomedical development phases relating to the received biomedical development data;

storing the received metadata in a database using a plurality of metadata structures, each of the plurality of metadata structures being specific to a different one of the plurality of biomedical development phases;

processing the metadata to generate links between two or more of the plurality of metadata structures to identify how biomedical development data received during one biomedical development phase interrelates with other biomedical development data received during another biomedical development phase;

identifying an adverse reaction; and determining whether the identified adverse reaction had been previously identified, wherein determining includes using one or more of the generated links, and wherein when the identified adverse reaction has not been previously identified, one or more recommendations for receiving metadata are generated to improve the likelihood of identifying any future adverse reactions.

14. The system of claim 13, further comprising instructions configured to cause the one or more processors to perform operations, including:

processing the biomedical development data and the metadata to generate a record of the biomedical development process for submission to the United States Food and Drug Administration (FDA).

15. The system of claim 13, further comprising instructions configured to cause the one or more processors to perform operations, including:

processing the metadata to generate links within the same metadata structure to identify interrelationships between biomedical development data received during the same biomedical development phase.

16. The system of claim 13, wherein the biomedical development data is received using one or more graphical interfaces, and wherein the one or more graphical interfaces include a product release graphical interface specific to a product release phase of the biomedical development process.

17. The system of claim 16, wherein the one or more graphical interfaces include an adverse reaction graphical interface that is configured to receive data that identifies information relating to adverse reactions in patients, and wherein information received by the adverse reaction graphical interface is used to identify interrelationships among adverse reactions in different patients.

18. The system of claim 16, wherein the one or more graphical interfaces include an FDA approval graphical interface specific to an FDA approval phase of the biomedical development process.

19. The system of claim 18, wherein the FDA approval graphical interface is configured to receive data corresponding to one or more areas of concern identified by the FDA.

20. The system of claim 16, wherein the one or more graphical interfaces include a discovery phase graphical interface specific to a discovery phase of the biomedical development process.

21. The system of claim 20, wherein the discovery phase graphical interface is configured to receive data that identifies how often test measurements were obtained during the discovery phase and any units associated with the test measurements.

22. The system of claim 21, wherein one or more interrelationships between the test measurements obtained during the discovery phase are identified.

23. The system of claim 20, wherein the discovery phase graphical interface is configured to receive data that specifies one or more data manipulations performed upon biomedical development data collected during the discovery phase.

24. The system of claim 23, wherein one or more interrelationships between the one or more data manipulations performed during the discovery phase are identified.

25. A computer-program product, tangibly embodied in a machine-readable storage medium, including instructions configured to cause a data processing apparatus to:

receive biomedical development data from each of a plurality of biomedical development phases;

receive metadata from each of the plurality of biomedical development phases relating to the received biomedical development data;

store the received metadata in a database using a plurality of metadata structures, each of the plurality of metadata structures being specific to a different one of the plurality of biomedical development phases;

process the metadata to generate links between two or more of the plurality of metadata structures to identify how biomedical development data received during one biomedical development phase interrelates with other biomedical development data received during another biomedical development phase;

identify an adverse reaction; and determine whether the identified adverse reaction had been previously identified, wherein determining includes using one or more of the generated links, and wherein when the identified adverse reaction has not been previously identified, one or more recommendations for receiving metadata are generated to improve the likelihood of identifying any future adverse reactions.

26. The computer-program product of claim 25, further comprising instructions configured to cause a data processing apparatus to:

process the biomedical development data and the metadata to generate a record of the biomedical development process for submission to the United States Food and Drug Administration (FDA).

27. The computer-program product of claim 25, further comprising instructions configured to cause a data processing apparatus to:

process the metadata to generate links within the same metadata structure to identify interrelationships between biomedical development data received during the same biomedical development phase.

28. The computer-program product of claim 25, wherein the biomedical development data is received using one or more graphical interfaces, and wherein the one or more graphical interfaces include a product release graphical interface specific to a product release phase of the biomedical development process.

29. The computer-program product of claim 28, wherein the one or more graphical interfaces include an adverse reaction graphical interface that is configured to receive data that identifies information relating to adverse reactions in patients, and wherein information received by the adverse reaction graphical interface is used to identify interrelationships among adverse reactions in different patients.

30. The computer-program product of claim 28, wherein the one or more graphical interfaces include an FDA approval graphical interface specific to an FDA approval phase of the biomedical development process.

31. The computer-program product of claim 30, wherein the FDA approval graphical interface is configured to receive data corresponding to one or more areas of concern identified by the FDA.

32. The computer-program product of claim 28, wherein the one or more graphical interfaces include a discovery phase graphical interface specific to a discovery phase of the biomedical development process.

33. The computer-program product of claim 32, wherein the discovery phase graphical interface is configured to receive data that identifies how often test measurements were obtained during the discovery phase and any units associated with the test measurements.

34. The computer-program product of claim 33, wherein one or more interrelationships between the test measurements obtained during the discovery phase are identified.

35. The computer-program product of claim 32, wherein the discovery phase graphical interface is configured to receive data that specifies one or more data manipulations performed upon biomedical development data collected during the discovery phase.

36. The computer-program product of claim 35, wherein one or more interrelationships between the one or more data manipulations performed during the discovery phase are identified.

* * * * *